(12) United States Patent
Pellinen et al.

(10) Patent No.: US 9,656,054 B2
(45) Date of Patent: May 23, 2017

(54) IMPLANTABLE ELECTRODE AND METHOD OF MAKING THE SAME

(71) Applicant: NeuroNexus Technologies, Inc., Ann Arbor, MI (US)

(72) Inventors: David S. Pellinen, Ann Arbor, MI (US); Mayurachat Ning Gulari, Ann Arbor, MI (US); Jamille Farraye Hetke, Brooklyn, MI (US); David J. Anderson, Ann Arbor, MI (US); Daryl R. Kipke, Dexter, MI (US); Rio J. Vetter, Van Buren Township, MI (US)

(73) Assignee: NEURONEXUS TECHNOLOGIES, INC., Ann Arbor, MI (US)

( * ) Notice: Subject to any disclaimer, the term of this patent is extended or adjusted under 35 U.S.C. 154(b) by 29 days.

(21) Appl. No.: 14/676,037

(22) Filed: Apr. 1, 2015

(65) Prior Publication Data

US 2015/0201855 A1  Jul. 23, 2015

Related U.S. Application Data

(62) Division of application No. 13/713,115, filed on Dec. 13, 2012, now Pat. No. 9,265,928, which is a division
(Continued)

(51) Int. Cl.
*A61N 1/05* (2006.01)
*H05K 1/11* (2006.01)
(Continued)

(52) U.S. Cl.
CPC ............ *A61N 1/05* (2013.01); *A61B 5/04001* (2013.01); *A61N 1/0551* (2013.01); *H05K 1/113* (2013.01);
(Continued)

(58) Field of Classification Search
CPC ...... A61N 1/05; A61N 1/0551; A61N 1/0529; A61B 5/04001; H05K 2201/09781; H05K 2201/2072
(Continued)

(56) References Cited

U.S. PATENT DOCUMENTS

| 3,847,687 A | 11/1974 | Davidsohn et al. |
| 3,921,916 A | 11/1975 | Bassous |

(Continued)

FOREIGN PATENT DOCUMENTS

| WO | 0112115 | 2/2001 |
| WO | 0236002 | 5/2002 |

(Continued)

OTHER PUBLICATIONS

IntSearch, "PCT/IB06/53700", Nov. 21, 2008, Nov. 21, 2008.
(Continued)

*Primary Examiner* — Michael Kahelin
*Assistant Examiner* — Minh Duc Pham
(74) *Attorney, Agent, or Firm* — Haynes and Boone, LLP; Taylor Merritt Meacham

(57) ABSTRACT

The implantable electrode system of the preferred embodiments includes a conductor, an interconnect coupled to the conductor, an insulator that insulates the interconnect, and an anchor that overlaps a peripheral edge of the electrode layer. The anchor is mechanically interlocked with the insulator. This structure is particularly useful with the electrode layer being a neural interface that is configured to provide either a recording and stimulating function.

18 Claims, 3 Drawing Sheets

Related U.S. Application Data of application No. 12/396,107, filed on Mar. 2, 2009, now Pat. No. 8,498,720.

(60) Provisional application No. 61/032,725, filed on Feb. 29, 2008.

(51) Int. Cl.
  *A61B 5/04* (2006.01)
  *H05K 1/03* (2006.01)
  *H05K 3/46* (2006.01)

(52) U.S. Cl.
  CPC ..... *A61B 2562/0209* (2013.01); *A61N 1/0529* (2013.01); *H05K 1/0393* (2013.01); *H05K 3/4644* (2013.01); *H05K 2201/09781* (2013.01); *H05K 2201/2072* (2013.01); *Y10T 29/49117* (2015.01)

(58) Field of Classification Search
  USPC .......................................................... 607/116
  See application file for complete search history.

(56) References Cited

U.S. PATENT DOCUMENTS

| | | | |
|---|---|---|---|
| 4,141,365 A | 2/1979 | Fischell et al. | |
| 4,166,469 A | 9/1979 | Littleford | |
| 4,306,562 A | 12/1981 | Osborne | |
| 4,455,192 A | 6/1984 | Tamai | |
| 4,461,304 A | 7/1984 | Kuperstein | |
| 4,465,482 A | 8/1984 | Tittel | |
| 4,762,135 A | 8/1988 | van der Puije et al. | |
| 4,886,065 A | 12/1989 | Collins | |
| 4,904,237 A | 2/1990 | Janese | |
| 5,108,819 A | 4/1992 | Heller et al. | |
| 5,180,376 A | 1/1993 | Fischell | |
| 5,207,709 A | 5/1993 | Picha | |
| 5,215,088 A | 6/1993 | Normann et al. | |
| 5,308,442 A | 5/1994 | Taub et al. | |
| 5,322,064 A | 6/1994 | Lundquist | |
| 5,385,635 A | 1/1995 | O'Neill | |
| 5,390,671 A | 2/1995 | Lord et al. | |
| 5,409,469 A | 4/1995 | Schaerf | |
| 5,496,360 A | 3/1996 | Hoffmann et al. | |
| 5,515,848 A | 5/1996 | Corbett et al. | |
| 5,524,338 A | 6/1996 | Martyniuk et al. | |
| 5,573,520 A | 11/1996 | Schwartz et al. | |
| 5,585,827 A | 12/1996 | Murakami | |
| 5,588,597 A | 12/1996 | Reinecke et al. | |
| 5,720,099 A | 2/1998 | Parker et al. | |
| 5,744,958 A | 4/1998 | Werne | |
| 5,800,535 A | 9/1998 | Howard | |
| 5,843,150 A | 12/1998 | Dreessen et al. | |
| 5,927,277 A | 7/1999 | Baudino et al. | |
| 5,938,694 A | 8/1999 | Jaraczewski et al. | |
| 5,975,085 A | 11/1999 | Rise | |
| 5,989,445 A | 11/1999 | Wise et al. | |
| 5,992,769 A | 11/1999 | Wise et al. | |
| 6,006,124 A | 12/1999 | Fischell et al. | |
| 6,016,449 A | 1/2000 | Fischell et al. | |
| 6,044,304 A | 3/2000 | Baudino | |
| 6,132,456 A | 10/2000 | Sommer et al. | |
| 6,181,569 B1 | 1/2001 | Chakravorty | |
| 6,205,361 B1 | 3/2001 | Kuzma et al. | |
| 6,228,111 B1 | 5/2001 | Törmälä et al. | |
| 6,324,433 B1 | 11/2001 | Errico | |
| 6,325,797 B1 | 12/2001 | Stewart et al. | |
| 6,374,143 B1 | 4/2002 | Berrang et al. | |
| 6,600,231 B2 | 7/2003 | Tominaga | |
| 6,618,623 B1 | 9/2003 | Pless et al. | |
| 6,829,498 B2 | 12/2004 | Kipke et al. | |
| 6,834,200 B2 | 12/2004 | Moxon et al. | |
| 6,878,643 B2 | 4/2005 | Krulevitch et al. | |
| 7,004,948 B1 | 2/2006 | Pianca et al. | |
| 7,006,859 B1 | 2/2006 | Osorio et al. | |
| 7,010,356 B2 | 3/2006 | Jog et al. | |
| 7,011,680 B2 | 3/2006 | Alt | |
| 7,089,059 B1 | 8/2006 | Pless | |
| 7,181,288 B1 | 2/2007 | Rezai et al. | |
| 7,343,205 B1 | 3/2008 | Pianca et al. | |
| 7,548,775 B2 | 6/2009 | Kipke et al. | |
| 7,871,707 B2 | 1/2011 | Laude et al. | |
| 7,914,842 B1 * | 3/2011 | Greenberg ........... A61N 1/0543 427/2.24 | |
| 7,941,202 B2 | 5/2011 | Hetke et al. | |
| 8,120,229 B2 | 2/2012 | Huang | |
| 2002/0052610 A1 | 5/2002 | Skakoon et al. | |
| 2002/0183817 A1 | 12/2002 | Van Venrooij et al. | |
| 2002/0198446 A1 | 12/2002 | Hill et al. | |
| 2003/0093129 A1 | 5/2003 | Nicolelis et al. | |
| 2003/0100823 A1 | 5/2003 | Kipke et al. | |
| 2003/0114906 A1 | 6/2003 | Booker, III et al. | |
| 2003/0187461 A1 | 10/2003 | Chin | |
| 2004/0006264 A1 | 1/2004 | Mojarradi et al. | |
| 2004/0102828 A1 | 5/2004 | Lowry et al. | |
| 2004/0106169 A1 | 6/2004 | Evans | |
| 2004/0199235 A1 | 10/2004 | Younis | |
| 2005/0004627 A1 | 1/2005 | Gibson et al. | |
| 2005/0021116 A1 | 1/2005 | He et al. | |
| 2005/0021117 A1 | 1/2005 | He et al. | |
| 2005/0137647 A1 | 6/2005 | Wallace et al. | |
| 2005/0222647 A1 | 10/2005 | Wahlstrand et al. | |
| 2006/0122677 A1 | 6/2006 | Vardiman | |
| 2006/0173263 A1 | 8/2006 | He et al. | |
| 2006/0247749 A1 | 11/2006 | Colvin | |
| 2006/0258951 A1 | 11/2006 | Bleich et al. | |
| 2006/0276866 A1 | 12/2006 | McCreery | |
| 2006/0282014 A1 | 12/2006 | Kipke et al. | |
| 2007/0073130 A1 | 3/2007 | Finch et al. | |
| 2007/0121305 A1 * | 5/2007 | Iijima ............... H01L 23/49833 361/760 | |
| 2007/0123765 A1 | 5/2007 | Hetke et al. | |
| 2007/0135885 A1 | 6/2007 | Risi | |
| 2008/0132970 A1 | 6/2008 | Barolat | |
| 2008/0208283 A1 | 8/2008 | Vetter et al. | |
| 2008/0255439 A1 | 10/2008 | Tang et al. | |
| 2008/0262584 A1 | 10/2008 | Bottomley et al. | |
| 2009/0099555 A1 | 4/2009 | Viohl et al. | |
| 2009/0102068 A1 | 4/2009 | Pellinen et al. | |
| 2009/0118806 A1 | 5/2009 | Vetter et al. | |
| 2009/0132042 A1 | 5/2009 | Hetke et al. | |
| 2009/0149934 A1 | 6/2009 | Ameri et al. | |
| 2009/0171421 A1 | 7/2009 | Atalar et al. | |
| 2009/0187196 A1 | 7/2009 | Vetter | |
| 2009/0240314 A1 | 9/2009 | Kong et al. | |
| 2009/0248118 A1 | 10/2009 | Bradley et al. | |
| 2009/0253977 A1 | 10/2009 | Kipke et al. | |
| 2009/0299167 A1 | 12/2009 | Seymour | |
| 2009/0312770 A1 | 12/2009 | Kozai et al. | |
| 2010/0030298 A1 | 2/2010 | Martens et al. | |
| 2010/0049499 A1 | 2/2010 | Hayashi | |
| 2010/0145216 A1 | 6/2010 | He et al. | |
| 2010/0145422 A1 | 6/2010 | Seymour et al. | |
| 2011/0093052 A1 | 4/2011 | Anderson et al. | |
| 2011/0154655 A1 | 6/2011 | Hetke et al. | |

FOREIGN PATENT DOCUMENTS

| | | |
|---|---|---|
| WO | 0241666 | 5/2002 |
| WO | 02096482 | 12/2002 |
| WO | 2005039696 | 5/2005 |
| WO | 2006138358 | 12/2006 |
| WO | 2007042999 | 4/2007 |
| WO | 2007089738 | 8/2007 |
| WO | 2008011721 | 1/2008 |
| WO | 2008038208 | 4/2008 |
| WO | 2008072125 | 6/2008 |
| WO | 2008109298 | 9/2008 |
| WO | 2009052423 | 4/2009 |
| WO | 2009052425 | 4/2009 |
| WO | 2010057095 | 5/2010 |

(56) References Cited

FOREIGN PATENT DOCUMENTS

| WO | 2011010257 | 1/2011 |
|---|---|---|
| WO | 2011046665 | 4/2011 |

OTHER PUBLICATIONS

IntSearch, "PCT/IB10/53250", Oct. 4, 2010, Oct. 4, 2010.
IntSearch, "PCT/US04/35030", Feb. 21, 2005, Feb. 21, 2005.
IntSearch, "PCT/US06/23139", Aug. 2, 2007, Aug. 2, 2007.
IntSearch, "PCT/US07/02465", Feb. 13, 2008, Feb. 13, 2008.
IntSearch, "PCT/US08/55025", Oct. 27, 2008, Oct. 27, 2008.
IntSearch, "PCT/US08/80364", Dec. 16, 2008, Dec. 16, 2008.
IntSearch, "PCT/US08/80366", Dec. 10, 2008, Dec. 10, 2008.
IntSearch, "PCT/US09164591", Jul. 21, 2010, Jul. 21, 2010.
IntSearch, "PCT/US10/44167", Sep. 27, 2010, Sep. 27, 2010.
Kaplan, et al., "A Novel Fabrication Method of Capillary Tubes on Quartz for Chemical Analysis Application", Industrial Microelectronics Center, PO Box 1084, S-164 21 Kista, Sweden, Fax +46 8 7505430, 1994.
Lin, et al., "Silicon-Processed Microneedles", IEEE Journal of Microelectromehani AL Systems vol. 8, No. 1, Mar. 1999.
Seymour, et al., "Neural Probe Design for Reduced Tissue Encapsulation in CNS", Science Direct Biomaterials 28 (2007) 3594-3607 Department of Biomedical Engineering, University of Michigan, 2212 Lurie Biomedical Engineering Building, 1101 Avenue, Ann Arbor, MI 48109-2099, USA, Mar. 27, 2007.
Seymour, et al., "The Insulation Performance of Reactibe Parylene Films in Implantable Electronic Devices", Biomaterials 30 (Sep. 2006) 6158-6167 Contents lists available at Science Direct, 2009.

\* cited by examiner

IMPLANTABLE ELECTRODE AND METHOD OF MAKING THE SAME

CROSS-REFERENCE TO RELATED APPLICATIONS

This application is a divisional of U.S. patent application Ser. No. 13/713,115, filed on Dec. 13, 2012, which is a divisional of U.S. patent application Ser. No. 12/396,107, filed on Mar. 2, 2009, now U.S. Pat. No. 8,498,720, which claims the benefit of U.S. Provisional Application Ser. No. 61/032,725, filed on 29 Feb. 2008, which is incorporated in its entirety by this reference.

TECHNICAL FIELD

This invention relates generally to the implantable electrodes field, and more specifically to an improved implantable electrode with an anchoring element and the method of making this improved system.

BACKGROUND

The adhesion of metals to polymers in conventional microfabrication techniques can be quite poor. Excellent adhesion, however, is critical for biomedical electrodes, which are implanted in tissue and are exposed to harsh environments. In such environments, poorly connected elements can lead to irreversible chemical reactions and possible device failure. The irreversible chemical reactions can include: 1) electrolysis of water, with consequent pH changes and gas formation, 2) electrode dissolution due to oxide formation of soluble metal complexes, and 3) corrosion or breakdown of passivity. In conventional electrodes, uneven charging across the electrode site is often seen. As an example, a much higher current density is typically seen in the perimeter of the electrode site than seen in the center, thus when the electrode is placed onto the tissue of the patient, the uneven charging may lead to unpredictable stimulation of the tissue of the patient. Uneven charging across the electrode site also leads to additional irreversible chemical reactions. In the case of higher current density along the perimeter than seen in the center, a relatively high potential difference between the perimeter of the electrode and the center of the electrode develops, leading to a higher chance of irreversible chemical reactions at the edge of the electrode site. This invention provides an improved and useful system and method for connecting layers within an electrode, increasing the reliability of an electrode, and decreasing the chance of irreversible chemical reactions within an electrode.

DESCRIPTION OF THE PREFERRED EMBODIMENTS

The following description of preferred embodiments of the invention is not intended to limit the invention to these embodiments, but rather to enable any person skilled in the art to make and use this invention.

Figure 1:
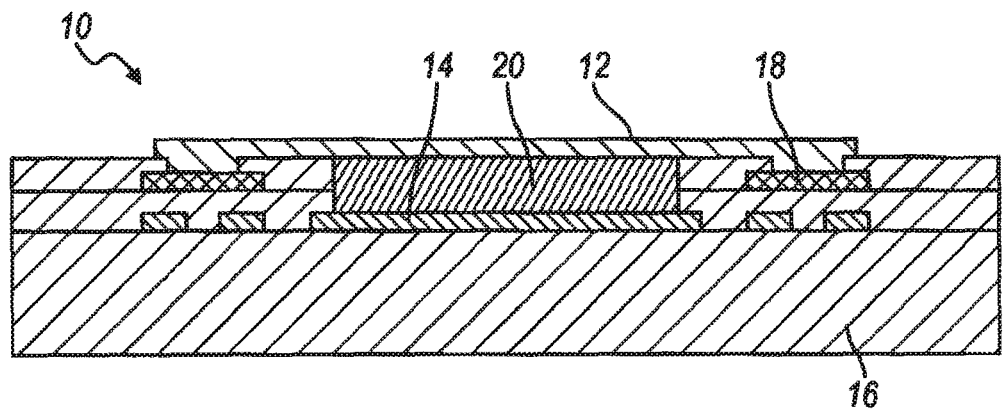
FIG. 1 is a cross-sectional view of the implantable electrode of the preferred embodiment including a first variation of the anchoring element.

As shown in FIG. 1, the implantable electrode 10 of the preferred embodiments includes an electrode site 12, an interconnect 14 coupled to the electrode site 12, an insulating element 16 that functions to insulate the interconnect 14, and an anchoring element 18 that functions to anchor the electrode site 12 to the implantable electrode 10. The implantable electrode 10 of the preferred embodiment is preferably designed for an implantable electrode lead system to interface with brain tissue, the implantable electrode 10 of the preferred embodiments, however, may be alternatively used in any suitable environment (such as the spinal cord, peripheral nerve, muscle, or any other suitable anatomical location) and for any suitable reason.

1. The Implantable Electrode

Figure 4:
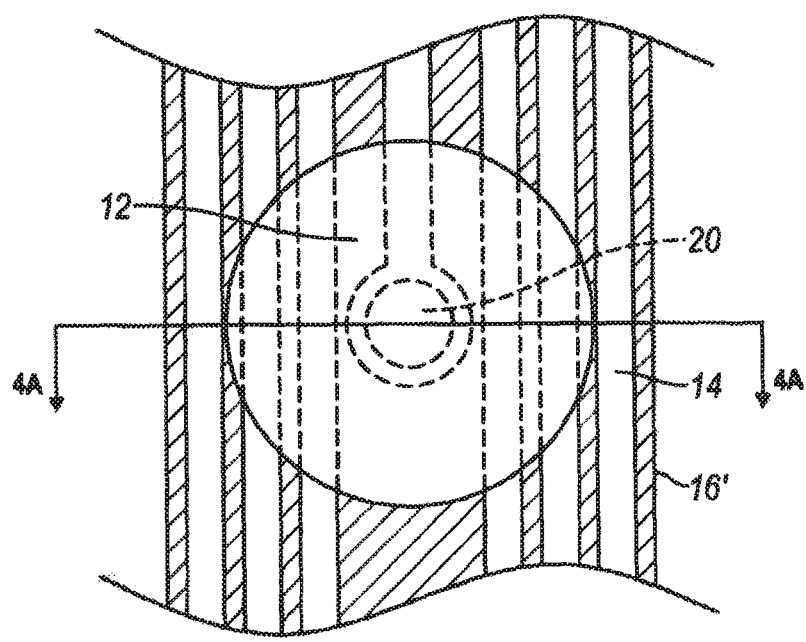
FIG. 4 is a top view and cross-sectional view of an implantable electrode.
Figure 4A:
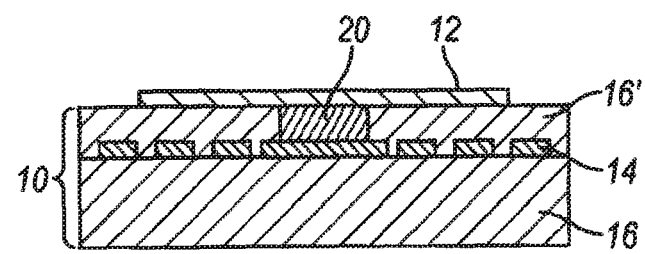
FIG. 4A is a cross-sectional view along line 4A-4A of FIG. 4.

As shown in FIGS. 1, 4 and 4A, the electrode site 12 of the preferred embodiment functions to record, stimulate, perform any other suitable function, or any combination thereof. The implantable electrode preferably includes a plurality of electrode sites 12, which may be independently tuned to record, stimulate, perform any other suitable function, or any combination thereof. Two or more electrode sites 12 may be grouped to form a larger composite site that enables tuning the neural interface region for recording and/or stimulation. The electrode site 12 is preferably a thin film metal, preferably made from gold, iridium, or platinum, but may alternatively be made from any suitable material.

The implantable electrode 10 of the preferred embodiments may further include a bond pad, which is electrically coupled to the electrode site 12 and functions to provide a point of contact to an external connector and/or device to provide a site from which recorded signals are accessed and/or to which stimuli are applied. The implantable electrode preferably includes a plurality of bond pads. The ratio of electrode sites 12 to bond pads is preferably 1:1, but may be any other suitable ratio. The bond pads are preferably gold, but may alternatively be any suitable material.

The implantable electrode 10 of the preferred embodiments may further include a plug 20 (also known as "leg"), which couples the electrode site 12 to the interconnect 14 and functions to transfer signals between the electrode site 12 and the interconnect 14. The implantable electrode preferably includes a plurality of plugs 20. The ratio of electrode sites 12 to plugs 20 is preferably 1:1, but may be any other suitable ratio. The plug 20 is preferably gold or platinum, but may alternatively be any suitable material.

As shown in FIGS. 1, 4 and 4A, the interconnect 14 of the preferred embodiment is coupled to the electrode site and functions to electrically couple the electrode site 12 to a bond pad or directly to an external connector and/or device and to transfer signals between the electrode site 12 and the bond pads, connector, and/or device. The implantable electrode preferably includes a plurality of interconnects 14. The ratio of electrode sites 12 to interconnects 14 is preferably 1:1, but may be any other suitable ratio. The interconnect 14 is preferably metal (such as platinum or gold) or polysilicon, but may alternatively be made out of any suitable material.

As shown in FIGS. 1, 4 and 4A, the insulating element 16 of the preferred embodiment functions to insulate the interconnect 14, preferably on the top and bottom side of the interconnect 14. The insulating element 16 is preferably one of several variations, and in some variations the insulating element 16 preferably includes multiple layers: a first layer 16 and a second layer 16'. In a first variation, where the interconnect 14 is preferably a metal such as platinum or gold, the insulating element 16 is preferably a polymer such as polyimide, parylene, or polydimethylsiloxane (PDMS). In a second variation, where the interconnect 14 is preferably polysilicon, the insulating element preferably includes a first layer 16 of inorganic dielectrics such as silicon dioxide or silicon nitride and a second layer 16' of a polymer. In a third variation, where the interconnect 14 is preferably polysilicon, the insulating element preferably includes a first layer 16 of inorganic dielectrics such as silicon dioxide or silicon nitride that are supported by a silicon substrate. The first layer 16 of inorganic dielectrics are preferably a tri-layer stack of silicon dioxide, silicon nitride, and silicon dioxide. Alternatives to the first layer 16 include silicon carbide and other polymers such as polyimide or parylene. The second layer 16' may be the same as the first layer, or may alternatively be a vapor deposited polymer such as parylene, Polytetrafluoroethylene (PTFE), other fluoropolymers, silicone, or any other suitable material. The second layer 16' preferably provides additional electrical insulation to leads.

Figure 2:
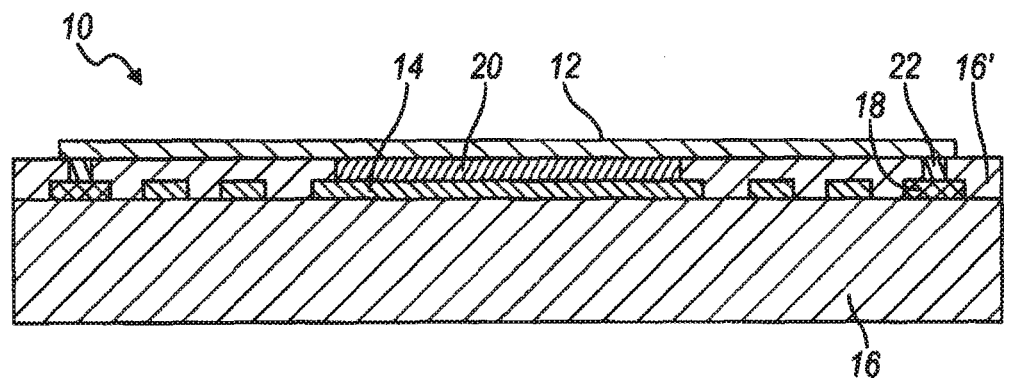
FIG. 2 is a cross-sectional view of the implantable electrode of the preferred embodiment including a second variation of the anchoring element.
Figure 3:
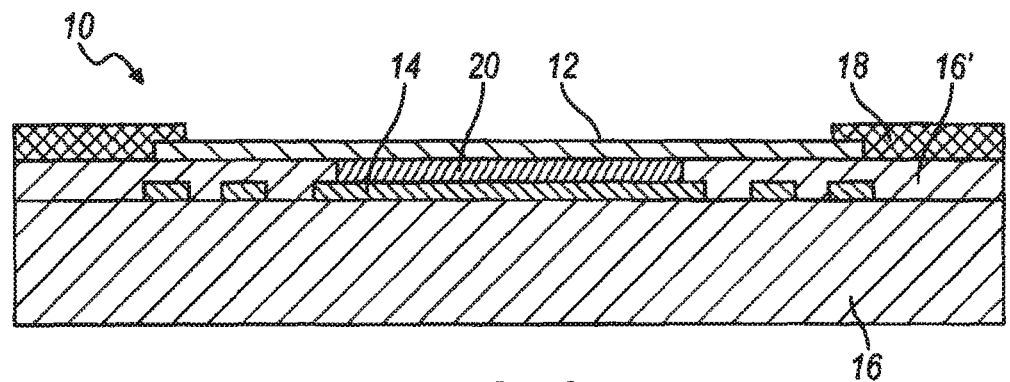
FIG. 3 is a cross-sectional view of the implantable electrode of the preferred embodiment including a third variation of the anchoring element.

As shown in FIGS. 1-3, the anchoring element 18 of the preferred embodiment functions to anchor the electrode site 12 to the implantable electrode 10. The anchoring element is preferably one of several variations. In a first variation, as shown in FIG. 1, the anchoring element 18 is a layer of metal. This metal layer is preferably located above the interconnect 14 such that it will not short or interfere with the interconnect 14. The metal layer is preferably located on the top surface of the second layer 16' of the insulation element 16. The metal electrode site 12 will adhere to the metal anchoring element 18. The strong metal-to-metal adhesion of the electrode site 12 to the anchoring element 18 preferably complements the adhesion of the electrode site 12 to the implantable electrode 10 (i.e. the top polymer surface). The anchoring element 18 in this variation is preferably buried in and/or under an additional layer 16" (preferably a polymer) of the insulation element 16 with a portion of the anchoring element 18 exposed to contact the electrode site 12. The exposed portion of the anchoring element 18 of this variation is preferably patterned to have a ring geometry that coincides with a perimeter portion of the electrode site 12. Alternatively, the exposed portion of the anchoring element 18 may form a semi-ring, may have multiple points, or may have any other suitable geometry. The geometry of the exposed portion of the anchoring element 18 may be defined by the anchoring element 18 and/or the additional layer 16" of the insulation element 16 and the pattern in which the anchoring element 18 is exposed.

In a second variation, as shown in FIG. 2, the anchoring element 18 is also a layer of metal, but this layer of metal is preferably located at the level of the interconnects 14 and is preferably insulated by the insulation element layers 16 and 16'. The metal electrode site 12 will adhere to the metal anchoring element 18. The strong metal-to-metal adhesion of the electrode site 12 to the anchoring element 18 preferably complements the adhesion of the electrode site 12 to the implantable electrode 10 (i.e. the top polymer surface). The anchoring element 18 of this variation preferably does not require the additional layer 16" of the insulation element 16, but rather, is preferably buried in the second layer 16' with a portion of the anchoring element 18 exposed to contact the electrode site 12. The anchoring element 18 of this variation is preferably patterned to have multiple points or "spots" that coincide with the perimeter portion of the electrode site 12, and are preferably positioned such that the multiple points will not cross over or connect adjacent interconnects 14. Alternatively, the exposed portion of the anchoring element 18 may form a semi-ring or may have any other suitable geometry. The anchoring element 18 of this variation may further include a plug 22, which couples the electrode site 12 to the anchoring element 18. The plug 22 is preferably gold or platinum, but may alternatively be any suitable material.

In a third variation, as shown in FIG. 3, the anchoring element 18 is a layer of an insulating material, such as a polymer, that functions to mechanically couple the electrode site 12 to the implantable electrode 10. The mechanical coupling of the electrode site 12 to the anchoring element 18 preferably complements the adhesion of the electrode site 12 to the implantable electrode 10 (i.e. the top polymer surface). The anchoring element 18 is preferably an additional layer of the insulation element 16. The anchoring element 18 is preferably located on the top surface of the second layer 16' of the insulation element 16. The electrode site 12 in this variation is preferably buried in and/or under the anchoring element 18 with a portion of the electrode site exposed. The exposed portion will record, stimulate, perform any other suitable function, or any combination thereof. The anchoring element 18 is preferably patterned to form a lip or a rim around the perimeter portion of the electrode site 12. Alternatively, the anchoring element 18 may have any other suitable geometry.

Figure 5A:
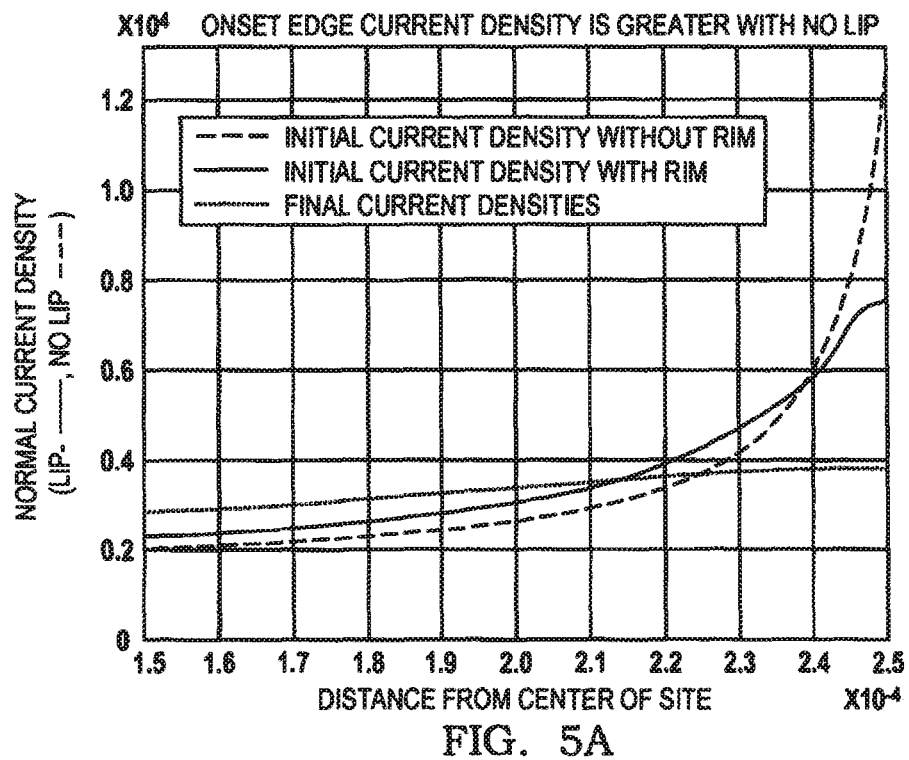
FIG. 5A is a graphical representation of the effect on current density across the electrode site of the preferred embodiment with the third variation of the anchoring element.
Figure 5B:
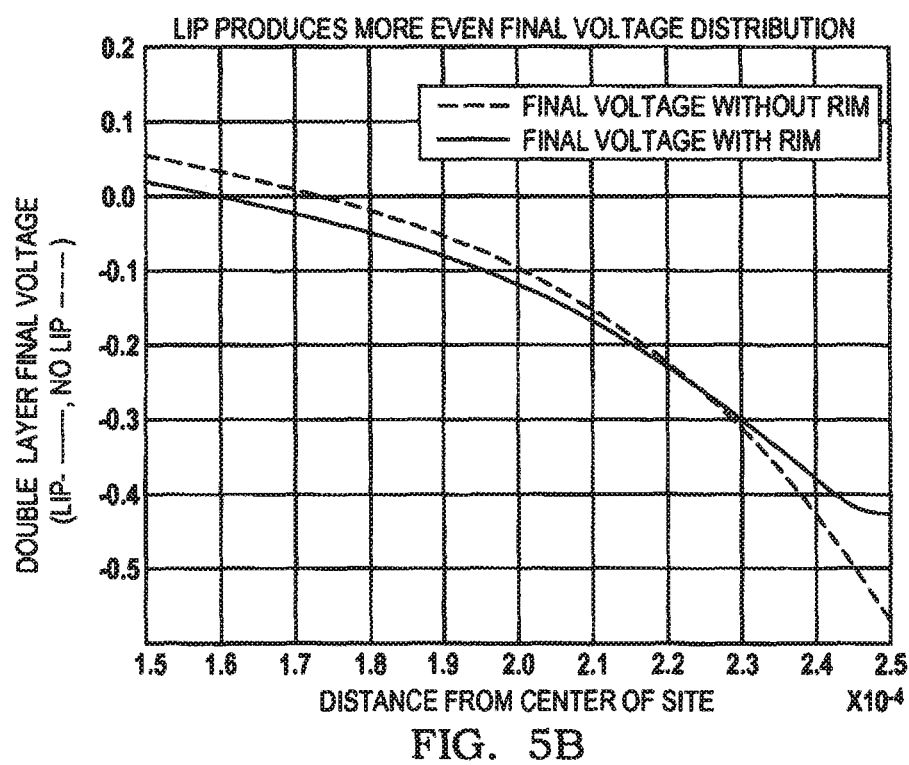
FIG. 5B is a graphical representation of the double layer final voltage across the electrode site of the preferred embodiment with the third variation of the anchoring element.

As shown in FIGS. 5A and 5B, the third variation of the anchoring element 18 also functions to normalize (or "make more uniform") the initial current distribution along the electrode site 12. In conventional implantable electrodes, as a stimulation pulse is sent to the electrode site 12, the initial current density along the electrode site 12 is not uniform. The current density along the perimeter of the electrode site 12 is higher than that at the center of the electrode site 12, leading to uneven changing across the electrode site 12 and creating a potential difference between the perimeter and the center of the electrode site 12. The difference in potential may lead to unpredictable stimulation of the tissue of the patient, such as charge spikes along the electrode site 12, and an increased chance of irreversible chemical reactions at the perimeter of the electrode site 12, thereby potentially releasing toxic products into the tissue of the patient and decreasing the effectiveness of the electrode 10. The third variation of the anchoring element 18 provides a raised lip along the perimeter of the electrode site 12. This raised lip has been shown to decrease the difference in initial current densities along the electrode site 12, as shown in FIG. 5A, leading to a more normalized final voltage potential distribution along the electrode site 12, as shown in FIG. 5B, increasing the reliability of the electrode and decreasing the chance of irreversible chemical reactions.

The anchoring element 18 of the third variation may alternatively be shaped to accommodate to the type of charge distribution desired across the electrode site 12. For example, a higher charge distribution may be desired in a first region than in a second region of the electrode site 12.

To achieve this, the raised lip may be thicker in the second region than in the first region. Alternatively, the raised lip of the anchoring element 18 may be of a uniform thickness around the perimeter of the electrode site 12 to achieve higher mitigation of the current density at the perimeter. However, any other arrangement of the anchoring element 18 suitable to regulate the charge distribution across the electrode site 12 may be used.

The anchoring element 18 of the third variation may also be shaped to accommodate to the type of mechanical interlock desired across the electrode site 12. For example, the raised lip of the anchoring element 18 may be shaped as an "X" across the electrode site 12, but may alternatively also be shaped as parallel ridges across the electrode site 12. However, any other arrangement of the anchoring element 18 suitable to provide an adequate mechanical interlock across the electrode site 12 may be used.

2. Method of Making the Implantable Electrode

The implantable electrode 10 of the preferred embodiment is preferably micro-machined using standard micro-fabrication techniques, but may alternatively be fabricated in any other suitable fashion. As shown in FIGS. 4 and 4A, the method of building an implantable electrode of the preferred embodiments includes building a first layer of the insulating element 16 S102, building an interconnect 14 S104, building a second layer 16' of the insulating element S106, removing a portion of the second layer 16' to expose a portion of the interconnect 14 S108, building a layer of conductive material to fill the second layer 16' S110, and building the electrode site 12 S112.

The method of building an implantable electrode with an anchoring element 18 of the preferred embodiments preferably includes additional and/or alternative steps to build the anchoring element 18 in one of several variations. In a first variation, as shown in FIG. 1, after Step S106 the method of the first variation includes building an anchoring element 18 S114, building a third layer 16" of the insulating element 16 S116, removing a portion of the third layer 16" to expose a portion of the anchoring element 18 and to expose a portion of the second layer 16' above the interconnect 14 S118, removing a portion of the second layer 16' to expose a portion of the interconnect 14 S108, building a layer of conductive material to fill the second layer 16' and the portion of the third layer 16" above the interconnect 14 S110', and building the electrode site 12 S112.

In a second variation, as shown in FIG. 2, the method of the second variation includes an alternative Step S104': building an interconnect 14 and an anchoring element 18, and an alternative Step S108': removing a portion of the second layer 16' to expose a portion of the interconnect 14 and the anchoring element 18. In a third variation, as shown in FIG. 3, the method of the third variation includes two additional steps after Step S112. Those steps include building an anchoring element 18 S120, and removing a portion of the anchoring element 18 to expose a portion of the electrode site 12 S122. The method is preferably designed for the manufacture of implantable electrodes, and more specifically for the manufacture of implantable electrodes with anchoring elements. The method and any variation thereof, however, may be alternatively used in any suitable environment and for any suitable reason.

Step S102, which recites building a first layer of the insulating element 16, functions to provide the base layer of the implantable electrode 10. The adding of material is preferably performed through any suitable deposition process that grows, coats, or transfers a material in any other suitable method. These deposition processes may include spinning and curing, physical vapor deposition (PVD), chemical vapor deposition (CVD), electrochemical deposition (ECD), molecular beam epitaxy (MBE) and more recently, atomic layer deposition (ALD), or any other suitable process.

Step S104 and S104', which recite building an interconnect 14 and building an interconnect 14 and an anchoring element 18 respectively, function to create the interconnects and/or the metal anchoring elements 18. This step is preferably performed by building a layer of material and then patterning the layer of material to form the interconnects 14 and/or the anchoring elements 18. The adding of material is preferably performed through any suitable deposition process that grows, coats, or transfers a material in any other suitable method. These deposition processes may include sputtering, evaporating, physical vapor deposition (PVD), chemical vapor deposition (CVD), electrochemical deposition (ECD), molecular beam epitaxy (MBE) and more recently, atomic layer deposition (ALD), or any other suitable process. The removal or patterning of material is preferably performed through reactive ion etching (RIE), but may alternatively be performed through any other suitable removal process, such as other dry etching methods, wet etching, chemical-mechanical planarization, or any combination thereof. The interconnects 14 and/or the anchoring elements 18 may alternatively be created by any suitable combination of deposition, removal, and or patterning.

Step S106, which recites building a second layer 16' of the insulating element is preferably performed in a similar fashion to Step S102 above.

Step S108, S108', and S118, which recite removing a portion of the insulating element to expose a portion of the interconnect 14, the anchoring element 18, and/or a lower layer of the insulating element function to expose a contact through the insulating element to the layer below. The removal or patterning of material is preferably performed through reactive ion etching (RIE), but may alternatively be performed through any other suitable removal process, such as other dry etching methods, wet etching, chemical-mechanical planarization, or any combination thereof. The interconnects 14 and/or the anchoring elements 18 may alternatively be created by any suitable combination of deposition, removal, and or patterning.

Step S110 and S110', which recite building a layer of conductive material to fill a layer of the insulating element, function to build a "plug" (also known as "leg") to fill the contact hole with conductive material and to form the plugs 20 and/or 22. The step is preferably performed through electroplating, but may alternatively be performed through any suitable deposition process that grows, coats, or transfers a material in any other suitable method.

Step S112, which recites building the electrode site 12, functions to create electrode site 12. This step is preferably performed by building a layer of material and then patterning the layer of material to form the electrode site 12. This step preferably uses a method to add material and then remove material as described in Step S104.

Step S114, which recites building an anchoring element 18, functions to create the metal layer anchoring element 18 of the first variation. This step is preferably performed by building a layer of material and then patterning the layer of material to form the anchoring element 18. This step preferably uses a method to add material and then remove material as described in Step S104.

Step S116 and Step S120, which recite building an anchoring element 18 and building a third layer 16" of the insulating element 16, function to create the anchoring element 18 of the third variation (which is preferably an insulating material) and to build the third layer of the insulating element, respectively. This is preferably performed in a similar fashion as described in Step S102.

Step S122, which recites removing a portion of the anchoring element 18 to expose a portion of the electrode site 12, functions to expose a contact through the anchoring element 18 to the electrode site 12. The removal or patterning of material is preferably performed through a deep reactive ion etching (DRIE), but may alternatively be performed through any other suitable removal process, such as other dry etching methods, wet etching, chemical-mechanical planarization, or any combination thereof. The interconnects 14 and/or the anchoring elements 18 may alternatively be created by any suitable combination of deposition, removal, and or patterning.

Although omitted for conciseness, the preferred embodiments include every combination and permutation of the various implantable electrodes, the various interconnects, the various insulation elements, the various anchoring elements, and the various methods of making the various implantable electrodes.

As a person skilled in the art will recognize from the previous detailed description and from the figures and claim, modifications and changes can be made to the preferred embodiments of the invention without departing from the scope of this invention defined in the following claim.

What is claimed is:

1. An implantable electrode, comprising:
    a) a first portion of an insulator layer;
    b) an electrically conductive interconnect layer supported by the first portion of the insulator layer, the interconnect layer comprising an interconnect peripheral edge providing an interconnect width or diameter extending between spaced apart first and second interconnect edges;
    c) an electrically conductive plug layer supported directly on an upper interconnect surface of the interconnect layer, the plug layer comprising a plug peripheral edge providing a plug width or diameter extending between spaced apart first and second plug edges;
    d) a second portion of the insulator layer supported on the first portion of the insulator layer and contacting the plug;
    e) an electrically conductive electrode layer supported directly on an upper plug surface of the plug layer, the electrode layer comprising an electrode peripheral edge providing an electrode width or diameter extending between spaced apart first and second electrode edges; and
    f) an anchor layer that overlaps only parts of the electrode layer including at least one of the first and second electrode edges, wherein the anchor layer is physically and electrically isolated from the interconnect layer and the plug layer by the insulator layer.

2. The implantable electrode of claim 1 wherein the anchor layer is of an electrically conductive material.

3. The implantable electrode of claim 1 wherein the anchor layer is of a material that acts as an electrical insulator.

4. The implantable electrode of claim 1 wherein the anchor layer is chemically bonded to the insulator layer.

5. The implantable electrode of claim 1 wherein the anchor layer is supported on an upper surface of the second portion of the insulator layer.

6. The implantable electrode of claim 1 wherein the anchor layer is spaced from the interconnect layer.

7. The implantable electrode of claim 1 wherein the anchor layer has a ring shape.

8. The implantable electrode of claim 1 wherein both the electrode layer and the anchor layer are of a metal material.

9. The implantable electrode of claim 1 wherein the electrode layer is chemically bonded to the plug layer.

10. The implantable electrode of claim 1 wherein the insulator layer is of a material that acts as an electrical insulator.

11. The implantable electrode of claim 1 wherein the second portion of the insulator layer is in an overlaying relationship with a portion of the upper interconnect surface.

12. The implantable electrode of claim 1 wherein the interconnect layer is of platinum or gold and the first and second portions of the insulator layer are a polymer selected from the group consisting of polyimide, parylene, and polydimethylsiloxane (PDMS).

13. The implantable electrode of claim 1 wherein the interconnect layer is polysilicon, the first portion of the insulator layer is an inorganic dielectric selected from silicon dioxide and silicon nitride, and the second portion of the insulator layer is a polymer selected from the group consisting of polyimide, parylene, and polydimethylsiloxane (PDMS).

14. The implantable electrode of claim 1 wherein the interconnect layer is of polysilicon, and wherein the first portion of the insulator layer is selected from the group consisting of silicon carbide, polyimide, and parylene.

15. The implantable electrode of claim 1 wherein the interconnect layer contacts the electrode layer spaced inwardly from the peripheral edge of the electrode layer.

16. The implantable electrode of claim 1 wherein the electrode layer is a neural interface that is configured to provide at least one function selected from the group consisting of recording and stimulating.

17. The implantable electrode of claim 1 wherein the second portion of the insulator layer contacts both the interconnect layer and the anchor layer and physically insulates the interconnect layer from the anchor layer.

18. The implantable electrode of claim 1 wherein the second portion of the insulator layer contacts both the plug peripheral edge and the interconnect peripheral edge.

* * * * *